United States Patent
Yang et al.

(10) Patent No.: US 9,474,272 B1
(45) Date of Patent: Oct. 25, 2016

(54) **MICROPROPAGATION OF ALEXANDRIAN LAUREL (*DANAE RACEMOSA* L)**

(71) Applicant: North Carolina A&T State University, Greensboro, NC (US)

(72) Inventors: Guochen Yang, Greensboro, NC (US); Zhongge Lu, Greensboro, NC (US)

(73) Assignee: North Carolina A&T State University, Greensboro, NC (US)

( * ) Notice: Subject to any disclaimer, the term of this patent is extended or adjusted under 35 U.S.C. 154(b) by 284 days.

(21) Appl. No.: 13/838,725

(22) Filed: Mar. 15, 2013

Related U.S. Application Data (60) Provisional application No. 61/614,336, filed on Mar. 22, 2012.

(51) Int. Cl.
*A01N 25/00* (2006.01)
*A01N 43/82* (2006.01)
*A01N 43/08* (2006.01)
*A01N 43/90* (2006.01)

(52) U.S. Cl.
CPC .............. *A01N 43/08* (2013.01); *A01N 43/82* (2013.01); *A01N 43/90* (2013.01)

(58) Field of Classification Search
None
See application file for complete search history.

(56) References Cited

U.S. PATENT DOCUMENTS 7,964,405 B2  6/2011  Laine et al. ................... 435/430

OTHER PUBLICATIONS

Yang et al.( Balanced seedling development of Alexandrian Laurel under different in vitro PGR treatments, Proceedings—Plant Growth Regulation Society of America (2011), 38th(y), 158-160 Coden: PPGRDG; ISSN: 0731-1664).*
Lu et al. (PSPS19 Expediting Production of Alexandrian Laurel through Micropropagation, Association of Research Directors, Inc. 16th Biennial Research Symposium, Apr. 9-13, 2011, Atlanta Marriott Marquis, Atlanta, GA, Program and Abstracts).*
"A Revised Medium for Rapid Growth and Bio Assays with Tobacco Tissue Cultures," Murashige and Skoog, Physiologia Plantarum, vol. 15, 1963.
"Plant Propagation Through Tissue Cultures," Murashige, Toshio, Ann. Rev. Plant Physiol. 1974, 25:135-66.
"Plant Cell and Organ Cultures As Horticultural Practices," Murashige, T., Plant Sciences Department University of California 1977.
"Commercially-Feasible Micropropagation of Mountain Laurel, Kalmia Latifollia, by Use of Shoot-Tip Culture," Lloyd and McCown, Intl. Plant Propagators' Society, vol. 30, 1980.
"New Technologies in Plant Tissue Culture," W. Jan Rowe, Agrigenetics Corp., 1986.
"Large Scale Tissue Culture Production for Horticultural Crops," Strode and Abner, Agri-Starts, Inc. 1986.
"In vitro culture of Vanhoutte's spirea explants from 'secondary cultures' and dormant stems forced in solutions containing plant growth regulators," Yang and Read, Plant Cell Tissue and Organ Culture 33: 25-30, 1993 (1991).
First experiences in Italy of IPM on ornamental cut foliage: Danae racemosa and Fatsia japonica, Sacco, et al., Integrataed control in Protected Crops, Mediterranean Climate, Albajes, R and E Sekerouglu (eds.) Abstract 2000.
In Vitro Response of Micropropagated Chestnut Shoot to Different Growth Regulators, Asante and Yang, HortScience, vol. 39(4), Jul. 2004.
Micropropagation of Indian laurel (Calophyllum inophyllum), a source of anti-HIV compounds, Thengane, et al. , Current Science, vol. 90, No. 10, May 25, 2006.
"Galax Seed Germination under Different in Vitro Conditions," Yang, Lu, et al., HortScience, vol. 42(4), Jul. 2007.
Tospoviruses Infecting Ruscus Racemosus (danae Racemosa) in Liguria, Bellardi, et al., J. of Plant Pathology, 2007, 89 (3, Suppl.) S27-S-68.
"In Vitro Callus Initiation of Guava," Yand and Lu, Proc. IS on Biotechnol. Temp. Fruit Crops & Trop. Species, Acta Hort. 738, ISHS 2007.
"Antinociceptive Properties of Extracts and Two Flavonoids Isolated from Leaves of Danae racemosa," Maleki-Dizaji, et al., Arch. Pharm Res. vol. 30, No. 12, 1536-1546, 2007.
"Sequential Additions of Plant Growth Regulators in the Forcing Solution Enhanced Propagation of Woody Plants," Yang, et al., IPGSA 19th Annual Meeting (2007), Abstracts, pp. 96-97, PS1006.
"Expediting Production of Alexandrian Laurel through Micropropagation," Yang and Lu, HortScience, vol. 43(4), p. 1213 #318; Jul. 2008.
"Efficient Germination Protocol Development for Alexandrian Laurel," Yang and Lu, ARD 2009, 1890 Research: Sustainable Solutions for the 21$^{st}$ Century.
In Vitro Protocol Development for Alexandrian Laurel, Yang, G., 2011 American Society for Horticultural Science, 2011 Annual Conference, Waikola, Hawaii, Poster #110.
"Expediting Production of Alexandrian Laurel through Micropropagation," Lu and Yang, Assn. of Research Directors, Inc., 16th Biennial Res. Symp., 1890 Research:Sustainable Solutions for Current and Emerging Issues, 2011.

(Continued)

*Primary Examiner* — Alton Pryor
(74) *Attorney, Agent, or Firm* — MacCord Mason PLLC (57) ABSTRACT

Alexandrian laurel (*Danae racemosa* L.) is a highly demanded evergreen shrub. However, seed germination often takes up to 12 to 18 months with a germination rate of only about 20%. Also, due to its slow-growth rate, it typically takes up to six years to produce a saleable one-gallon size plant. Germinating seeds in the presence of cytokinins and/or auxins increased in vitro shoot multiplication and seedling quality enhancement. Benzyladenine was found to balance seedling development by simultaneously accelerating shoot growth and slowing down root growth, whereas thidiazuron significantly promoted shoot multiplication and proliferation by producing 5-30 shoots per seed.

10 Claims, 5 Drawing Sheets
(5 of 5 Drawing Sheet(s) Filed in Color)

(56) References Cited

OTHER PUBLICATIONS

"Balanced Seedling Development of alexandrian Laurel Uner Different in Vitro PGR Treatments," Yang and Lu, Dept. of Nat. Resources & Env. Design, NC A&T Univ, . 2011.

"Expediting Propagation Through Additions of Plant Growth Regulators in the Forcing Solution," Yang and Read, Proc. of the 35th Annual Meeting of Plant Growth Reg. Soc. of America, San Fran. CA 2008.

Expediting Alexandrian Laurel Production Through Micropropagation; Yang and Ibrahim, NC A&T State University Mar. 2010.

Expediting Alexandrian Laurel Production Through Micropropagation; Yang, NC A&T State University, Greenboro, NC 27411, Mar. 2013.

* cited by examiner

MICROPROPAGATION OF ALEXANDRIAN LAUREL (*DANAE RACEMOSA* L)

STATEMENT AS TO RIGHTS TO INVENTIONS MADE UNDER FEDERALLY SPONSORED RESEARCH OR DEVELOPMENT

Work described herein may have been supported in part by USDA accession number 0219532, Project number NCX-244-5-10-130-1. The United States Government may therefore have certain rights in the inventions.

FIELD

The present application relates to the micropropagation of Alexandrian laurel (*Danae racemosa* L.).

BACKGROUND

Alexandrian laurel (*Danae racemosa* L.) is a highly desirable species but is difficult to germinate and propagate. It is one of the finest of broadleaf, dark evergreen shrubs with branches arching to three feet in height and four feet wide. The shrub is an excellent choice for both woodland and shade gardens and is highly demanded by landscape architects and designers. In addition, there is some interest in the antinociceptive (i.e. increasing tolerance for pain) properties of extracts and flavonoids isolated from leaves of Alexandrian laurel. Currently, United States is importing almost all Alexandrian laurel cut foliage for flower arrangement from Italy and other countries.

Once established in proper growth conditions, Alexandrian laurel requires little intervention, such as disease and insect control, watering, and wild animal resistance. Normal propagation for this species is by seeds and division. Conventional seed germination takes up to a year and half with a success rate of only about 20%. It typically takes up to six years to produce a one-gallon size plant, such as the size generally sold by greenhouses. The long period of germination and slow growth adversely affect its commercial availability.

Agricultural biotechnology is important for the farming community in agriculture, horticulture and forestry. Agbiotech approaches include in vitro culture techniques, including tissue culture and micropropagation. The in vitro techniques are especially notable in horticulture because of the demonstrated potential for mass production of targeted plant materials. In vitro culture techniques generally involve placing a small piece of plant material in a container such as a test tube, a Petri dish, or a baby food jar containing culture medium with balanced nutrients. Due to the space savings associated with in vitro culture methods, they can reduce energy costs associated with growing young plants. This technique can be useful for mass production of plants with unique characteristics and plants that are difficult to propagate, including those with low germination rates. However, this technique is generally species-specific and detailed steps and formulae for each plant species require intensive scientific research.

Micropropagation can be cost-effective and useful for farmers and nursery owners with limited resources, as once they learn basic aseptic techniques, these growers can use micropropagation techniques to follow scientifically proven processes to produce a highly desirable plant. This technique can also produce disease-free plants that can be used as disease-free seedstock, which is particularly useful for horticultural crops. However, plant species with unique quality and/or characteristics are often difficult to propagate; this is true for woody plant species, such as Alexandrian laurel.

A number of issues remain in the propagation of Alexandrian laurel, including: (a) a limited numbers of seeds available for commercial sale, due to the slow growth of the plant; (b) very low multiplication rate, as only one seedling grows from each seed; and (c) unbalanced seedling growth observed where the seedlings have with too much root growth and too little shoot growth.

Thus, an efficient propagation protocol to produce high quality Alexandrian laurel plants in a shorter germination period is needed. Also needed is a process that allows for efficient germination, enhancement of seedling quality, and the production of multiple seedlings per a single seed.

SUMMARY

The present application is directed to a method for the propagation of Alexandrian laurel, comprising: (a) germinating an Alexandrian laurel seed using in vitro techniques; (b) culturing the germinated seed in a growth medium comprising a purin-based cytokinin plant growth regulator until a plantlet having at least one root and one shoot is observed; and (c) acclimatizing the plantlet in soil. In one variation, the at least one root and one shoot is observed after about 2 weeks and the plantlet is transferred to soil within at least one week.

The present application is further directed to a method for the propagation of Alexandrian laurel, comprising: (a) germinating an Alexandrian laurel seed in a germination induction medium comprising a gibberellin; (b) culturing the germinated seed in a growth induction medium comprising a purin-based cytokinin plant growth regulator for no more than about 8 weeks, wherein the resulting plantlet has a viable shoot and root; (c) acclimatizing the plantlet in soil. In one variation, the germinated seed is grown in a growth induction medium for no more than about 4 weeks.

The present application is further directed to a method for the propagation of Alexandrian laurel, comprising: (a) germinating an Alexandrian laurel seed in a germination induction medium including about 4 ppm to about 40 ppm gibberellins; (b) culturing the germinated seed in a growth induction medium comprising at least one a purin-based cytokinin plant growth regulator at a concentration of between about 1 µM and about 50 µM for between about two weeks and about 8 weeks to grow a plantlet from the seed and (c) acclimatizing the plantlet in soil.

The present application is further directed to a method for the propagation of Alexandrian laurel, comprising: (a) germinating an Alexandrian laurel seed using in vitro techniques; (b) culturing the germinated seed in a growth medium comprising a phenylurea cytokinin plant growth regulator to yield multiple shoots and at least one root from a single seed; (c) separating the multiple shoot crown from the root(s); (d) culturing the crown in a basic medium comprising basal medium with optional plant growth regulator; (e) isolating an individual shoot from the crown; (f) culturing the individual shoot in a root growth medium yielding a plantlet having a viable shoot and a root; and (f) acclimatizing the plantlet in soil.

The present application is also directed to a method to produce multiple seedlings of Alexandrian laurel from one seed, the method comprising: (a) germinating an Alexandrian laurel seed in a germination induction medium including a gibberellin; (b) culturing the germinated seed in a growth medium comprising a phenylurea cytokinin plant growth regulator for a sufficient time to grow two or more visible shoots and at least one root; (c) separating the multiple shoot crown from the root system; (d) culturing the multiple shoot crown in a growth medium comprising a basal medium, and optionally a sugar compound and/or a plant growth regulator; (e) separating an individual shoot from the multiple shoot crown; (f) culturing an individual shoot in a root growth medium comprising an auxin plant growth regulator yielding a plantlet having balanced growth of a viable shoot and a root; (g) acclimatizing the resulting plantlet in soil. Steps (d), (e) and (f) can be repeated to yield multiple plantlets from a single seed.

In another aspect, the present application discloses a method to produce multiple seedlings of Alexandrian laurel from one seed, the method comprising: (a) germinating an Alexandrian laurel seed in a germination induction medium including gibberellic acid at a concentration of about 4 ppm to about 15 ppm; (b) culturing the germinated seed in a growth induction medium including between about 1 µM and about 20 µM thidiazuron, wherein the culturing results in two or more shoots and at least one root visible from the seed; (c) separating the multiple-shoot crown from the root(s); (d) culturing the separated multiple-shoot crown in a basic medium; (e) isolating an individual shoot from the multiple shoot crown and culturing the shoot in a root growth medium including a plant growth regulator to yield a plantlet having a viable shoot and root; and (f) acclimatizing the plantlet in soil.

In yet another aspect, the present application discloses a method of propagating multiple Alexandrian laurel plantlets from a single seed, the method comprising: (a)disinfecting an Alexandrian laurel seed; (b) germinating the seed for at least about eight weeks in a germination induction medium including gibberellic acid at a concentration of about 4 ppm to about 15 ppm; (c) culturing the germinated seed for at least about four weeks in a growth induction medium including between about 1 µM and about 20 µM thidiazuron, wherein the culturing results in at least one root and a multiple shoot crown comprising a first individual shoot and a second individual shoot visible from the seed; (d) separating the first individual shoot and the second individual shoot from the root(s); (e) culturing the first individual shoot and the second individual shoot in a root growth medium including a plant growth regulator to yield a first plantlet and a second plantlet, each plantlet having a viable shoot and root; and (f) acclimatizing the first and second plantlets in soil.

These and other objects and aspects of the present inventions will become apparent to those skilled in the art after a reading of the following description of the disclosure when considered with the Figures.

BRIEF DESCRIPTION OF THE FIGURES

The patent or application file contains color photographs. Copies of this patent or patent application publication with color photographs will be provided by the Office upon request and payment of the necessary fee.

It will be understood that the Figures are for the purpose of describing an embodiment of the inventions and are not intended to limit the inventions thereto.

DETAILED DESCRIPTION

In accordance with the present application and as used herein, the following terms are defined with the following meanings, unless explicitly stated otherwise.

As used herein, 'Alexandrian laurel' refers to *Danae racemosa* L.

As used herein, a 'germination induction medium' refers to a substrate preferentially formulated for germination. Such a formulation may include plant growth regulators known to encourage germination, such as gibberellins.

As used herein 'germinated seed' refers to a seed where the seed coat is cracked and at least one root and/or one cotyledon leaf can be seen.

As used herein, a 'cotyledon' or 'cotyledon leaf' is a leaf visible from a germinated seed. A cotyledon is distinguished from a true leaf growing as part of a shoot, which appears after germination.

As used herein, a 'basal medium' or "plant growth medium" refers to a plant growth medium comprising supplements, generally as defined in the related literature references. Such basal media include, but are not limited to, MS base medium (Murashige T and Skoog F (1962) A revised medium for rapid growth and bio-assays with tobacco tissue cultures. Physiol Plant 15(3): 473-497), LS medium (Linsmaier and Skoog, 1965 "Organic growth factor requirements of tobacco tissue cultures" Physiol. Plant. 18:100-127), Woody Plant Medium ("WPM" Lloyd, G & McCown, B. H. 1981 *Proc. Int. Plant Prop. Soc.* 30:421-427), White's medium (White, P. R. (February 1939). "Potentially unlimited growth of excised plant callus in an artificial nutrient". American Journal of Botany 26 (2): 59-4), SH medium (Schenk, R. U. and A. C. Hildebrandt, 1972, Medium and Techniques for Induction and Growth of Monocotyledonous and Dicotyledonous Plant Cell Cultures, Can. J. Bot. 50:199-204) and DWK (Hammatt and Grant, 1998 "Shoot regeneration from leaves of *Prunus serotina* Ehrh. (black cherry) and *P. avium* L. (wild cherry)" Plant Cell Rep. 17: 526-530).

As used herein "supplemented WPM" refers to Woody Plant Medium supplemented with one or more of about 0.7% agar and about 3% sucrose, optionally with a growth regulator. Generally the pH of supplemented WPM is about 6.

As used herein, "rooting medium" or "root growth medium" refers to a basal medium preferentially formulated for root growth. Such a formulation may include plant growth regulators known to encourage root growth, such as, for example, auxins.

As used herein "BA-supplemented WPM" and "TDZ-supplemented WPM" refer to supplemented WPM further comprising identified amounts of BA and TDZ respectively. Analogously "IBA-supplemented MS" refers to supplemented MS medium further comprising identified amounts of indole-3-butyric acid (IBA).

As used herein, a 'plantlet' refers to a plant that has at least one true leaf and at least one root, wherein the true leaf is not the cotyledon observed during germination, or has at least one shoot and one root. Plantlets can be found for example, after the germination of a seed, wherein each of a shoot and a root are observed, or resulting from the growth of a root from a viable shoot in a root growth medium. A shoot containing one true leaf is generally referred to as a "viable shoot." In one variation, a plantlet has balanced growth of the at least one shoot and the at least one root, for example, wherein each is at least about 1.5 cm in length. Alternately the plantlet comprises both a root and a shoot and can be 3-4 cm in overall length.

As used herein "balanced growth" of a root and a shoot refers to substantially equal growth lengths of the two components. Typically the root and the shoot have the same length, or are within at least about 30% of the other in length.

As used herein, a 'radical' refers to the first root that comes out of a germinated seed.

DETAILED DESCRIPTION

As disclosed herein, in vitro techniques for seed germination were combined with micropropagation and the use of a number of plant growth regulators. Conditions and culture media that can be suitably used in plant micropropagation are described in "Plant Propagation by Tissue Culture, Handbook and Directory of Commercial Laboratories, eds. Edwin F George and Paul D Sherrington, Exegetics Ltd, 1984.

Examples of plant growth media or basal media include MS base medium, LS medium, Woody Plant Medium, White's medium, SH medium, and DWK. Natural products, such as potatoes have also been used as base media, after baking or microwaving the potato.

Plant growth media also generally contain a gelling agent, or substrate, such as the polysaccharides agar or gellan gum, (GELRITE®, APPLIEDGEL®, or PHYTAGEL®). Alternative support materials include, but are not limited to, perforated cellophane, filter paper bridges, filter paper wicks, polyurethane foam, and polyester fleece. Generally the substrate is agar.

Additional compounds that may be used as a supplement in the propagation medium according to the present application include suitable carbon sources. Such carbon sources include sugar compounds, for example, sucrose, glucose, fructose, lactose, galactose, rafinose, maltose, and starch or a combination thereof.

Further compounds that may be suitably used as a supplement for the initiation and/or growth media include but are not limited to: vitamins, such as thiamin (B1), nicotinic acid, pyridoxine (B6), and inositol and its isomers such as myo-inositol, biotin, folic acid, ascorbic acid, pantothenic acid, vitamin E, riboflavin, and p-aminobenzoic acid. Amino acids, for example, L-glutamine, L-asparagine, and adenine, as well as amino acid mixtures (e.g., casein hydrolysate) can also be added to initiation and/or growth media. Additional components may include cysteine or polyvinyl pyrrolidone (PVP).

Another component commonly used in rooting media is activated charcoal. Without being bound by theory, activated charcoal is generally believed to darken the medium to mimic growth in soil, and to absorb compounds that inhibit the micropropagation of plants in a culture medium.

As generally summarized in Scheme 1, the present application discloses methods for the micropropagation of a single Alexandrian laurel seed yielding either a plant or multiple Alexandrian laurel plants.

Scheme 1. Micropropagation of Alexandrian laurel

Generally in preparation for growth under aseptic conditions, seeds are disinfected, for example in a bleach solution optionally containing Tween (6-8 drops per liter bleach) or in solutions comprising ethanol (70%-75% in water), methanol (70%-75% in water) or combination thereof (total 70%-75% in water). Other solutions for disinfecting seeds that are known to those of skill in the art may also be suitable. The disinfected seeds are then rinsed and transferred to a container containing a growth medium including agar and plant growth regulators. The pH of the growth medium is usually between about 5 and about 6.5, desirably between about 5.3 and about 6.3. The pH is desirably adjusted to between about 5.5 and about 5.8. The growth medium can then be sterilized, such as via autoclaving or membrane filtration or other sterilization methods known to those of skill in the art.

Initially, seeds are germinated in an agar medium comprising a gibberellin, such as gibberellic acid ($GA_3$), gibberellin A1 (GA1), ent-Gibberellane, etc. Usually the growth regulator is used at a concentration of about 5 ppm to about 40 ppm or about 10 ppm, 20 ppm, 30 ppm or 40 ppm. Typically, $GA_3$ is used at a concentration of between about 4 ppm and about 15 ppm. Generally, seeds are kept in the supplemented germination medium for between about one week and about twenty weeks before a root and/or single leaf is observed or alternately when both a root and a true leaf (as part of a shoot) are observed. In another variation, the seeds can be kept in the medium for between about two weeks and about sixteen weeks. In another variation, the seeds can be kept in the medium for between about three weeks and about fourteen weeks. Generally the seeds are kept in the medium for between about 8 weeks and 12 weeks. In yet another variation, the seeds are kept in the medium for between about 4 weeks and 8 weeks. Alternately, the seeds are kept in the medium for 4 weeks, 5 weeks, 6 weeks, 7 weeks, 8 weeks, 9 weeks, 10 weeks, 11 weeks, or 12 weeks.

Following germination, seeds are transferred to a supplemented growth medium comprising a base plant growth medium (e.g. WPM, MS, or LS media), a sugar compound, and agar and optionally comprises one or more plant growth regulators.

Compounds which belong to the cytokinin family of growth regulators and which may be used according to the present application as a suitable stimulator in the growth medium may be any compound selected from the group consisting of purin-based cytokinins such as, for example, kinetin (N-(2-furanylmethyl)-1H-puring-6-amine), zeatin (6-(4-hydroxy-3-methy-trans-2-butenylamino)purine), 6-benzylamino purine (BAP or benzyladenine, BA); 6-(benzylamino)-9-(2-tetrahydropyrany-10-9h-purine (PBA); or (6-(γγ-dimethyl-allylamino) purine (2iP); and cytokinins based on substituted phenyl ureas for example, [1-phenyl-3-(1,2,3-thidiazol-5-yl)urea] (thidiazuron or TDZ), diphenylurea, and N-(2-Chloro-4-pyridyl)-N1-phenylurea (CPPU), or any other compound belonging to the cytokinin family of growth regulators. Naturally occurring compounds, including adenine, which has a base structure similar to that of the cytokinins and has shown cytokinin-like activity in some cases, have also been used as growth regulators. Cytokinins are used in concentrations between about 0.1 μM and about 50 μM. In one variation the concentration is between about 0.5 μM and about 40 μM or between about 1 μM and about 30 μM or between about 2 μM and about 25 μM or even between about 5 μM and about 15 μM, or between about 0.5 μM and about 15 μM or between about 1 μM and about 20 μM. For example cytokinin concentration can be about 0.1 μM, about 0.2 μM, about 0.3 μM, about 0.4 μM, about 0.5 μM, about 0.75 μM, about 1 μM, about 1.5 μM, about 2 μM, about 3 μM, about 4 μM, about 5 μM, about 6 μM, about 7 μM, about 7.5 μM, about 8 μM, about 9 μM, about 10 μM, about 11 μM, about 12 μM, about 12.5 μM, about 13 μM, about 14 μM, about 15 μM, about 17.5 μM, about 20 μM, about 25 μM, about 30 μM, about 35 μM, about 40 μM, about 45 μM, or about 50 μM.

Compounds which belong to the auxin family of growth regulators and which may be used according to the present application as a suitable supplement in the rooting medium may be any compound selected from the group consisting of indole-3-butyric acid (IBA); α-naphthaleneacetic acid (NAA); indole-3-acetic-acid (IAA); 4-chloroindole-3-acetic acid (4-Cl-IAA); 4-chlorophenoxyacetic acid (4-CPA, PCPA); (2,4,5-trichlorophenoxy)acetic acid (2,4,5-T); 3,6-dichloro-2-methoxybenzoic acid (Dicamba); and 4-amino-3,5,6-trichloropicolinic acid (Picloram) or any other compound belonging to the auxin family of growth regulators. Generally auxins are used in concentrations between about 0.1 μM and about 50 μM. In one variation the concentration is between about 0.5 μM and about 40 μM or between about 1 μM and about 30 μM or between about 2 μM and about 25 μM or even between about 5 μM and about 15 μM, or between about 0.5 μM and about 15 μM. For example cytokinin concentration can be about 0.1 μM, about 0.2 μM, about 0.3 μM, about 0.4 μM, about 0.5 μM, about 0.75 μM, about 1 μM, about 1.5 μM, about 2 μM, about 3 μM, about 4 μM, about 5 μM, about 6 μM, about 7 μM, about 7.5 μM, about 8 μM, about 9 μM, about 10 μM, about 11 μM, about 12 μM, about 12.5 μM, about 13 μM, about 14 μM, about 15 μM, about 17.5 μM, about 20 μM, about 25 μM, about 30 μM, about 35 μM, about 40 μM, about 45 μM, or about 50 μM.

The present application is directed to a method for the propagation of Alexandrian laurel, comprising: (a) germinating an Alexandrian laurel seed using in vitro techniques; (b) culturing the germinated seed in a growth induction medium comprising a purin-based cytokinin plant growth regulator until a plantlet having balanced growth of at least one root and one true leaf is observed; and (c) acclimatizing the plantlet in soil. In one variation, the balanced growth of at least one root and one shoot is observed after about two weeks and the plantlet is transferred to soil within at least one week.

The present application is further directed to a method for the propagation of Alexandrian laurel, comprising: (a) germinating an Alexandrian laurel seed in a germination induction medium comprising a gibberellin; (b) culturing the germinated seed in a growth induction medium comprising a purin-based cytokinin plant growth regulator for no more than about 8 weeks, wherein the resulting plantlet has balanced growth of a viable shoot and root; (d) acclimatizing the plantlet in soil. In one variation, the germinated seed is grown in a growth induction medium for no more than about 4 weeks. In one embodiment, the seed is germinated for at least about two weeks. In another embodiment, the seed is germinated for about 10 weeks.

In one aspect, the present application discloses a method for the propagation of Alexandrian laurel, comprising: (a) germinating an Alexandrian laurel seed in a germination induction medium including about 4 ppm to about 40 ppm gibberellins; (b) culturing the germinated seed in a growth induction medium including at least one purin-based cytokinin plant growth regulator at a concentration of between about 1 μM and about 20 μM for between about two weeks and about eight weeks to grow a plantlet from the seed; and (c) acclimatizing the plantlet in soil.

In one embodiment, the growth induction medium comprises agar. In another embodiment, the gibberellin is gibberellic acid at a concentration of between about 4 ppm and about 15 ppm, typically about 10 ppm. In another embodiment, the purin-based cytokinin is selected from the group consisting of 6-benzylaminopurine, kinetin, 2-isopentyladenine, zeatin and mixtures thereof. In one variation, the concentration of the purin-based cytokinin is between about 0.1 mg/L and about 3 mg/L. Generally the concentration is about 0.1 mg/L, about 0.5 mg/L, about 1.0 mg/L, about 1.5 mg/L, about 2.0 mg/L, about 2.5 mg/L or about 3.0 mg/L. In one alternative, the purin-based cytokinin is 6-benzylaminopurine ("BA") at a concentration between about 1 mg/L and about 3 mg/L In one alternative, BA at a concentration of between about 0.5 mg/L and about 1.5 mg/L is used in combination with kinetin at a concentration between about 0.1 mg/L and about 1.5 mg/L. In another alternative, the cytokinin is kinetin or zeatin, each at a concentration of between about 0.1 mg/L and about 3 mg/L or a combination thereof at a total concentration of between about 0.5 mg/L and about 3 mg/L. In yet another variation, the growth induction medium comprises kinetin at a concentration of between about 0.1 mg/L and about 3 mg/L in combination with a phenyl-urea cytokinin at a concentration of between about 0.1 mg/L and 3 mg/L. Typically the phenyl-urea cytokinin is thidiazuron and the cumulative concentration of the plant growth regulators in the medium is between about 0.1 and about 3 mg/L; usually the overall concentration of the plant growth regulator is about 0.2 mg/L, about 0.5 mg/L, about 0.6 mg/L, about 1.0 mg/L, about 1.5 mg/L, about 2.0 mg/L, about 2.5 mg/L or about 3 mg/L.

In one aspect, after the germinated seed grows in supplemented plant growth medium comprising a purin-based cytokinin for a length of time sufficient to grow a balanced root and viable shoot, the resulting plantlets are transferred out of the supplemented medium. For example, after between about 2 weeks and about 8 weeks in the supplemented plant growth medium, the plantlets are transferred. Generally after about 4 weeks the plantlets are transferred. In one embodiment, the plantlets are transferred to soil to acclimatize in a greenhouse or nursery setting. In one embodiment, the plantlet is grown in the supplemented plant growth medium until a true leaf appears, which can, but does not have to, correspond to a root about 2 cm to about 3 cm in length. Generally, the plantlet is grown until the root and shoot have roughly equal growth, for example when the plantlet size is between about 3 cm and about 4 cm. At that point in growth, it is propitious to transfer the plantlet to soil to acclimatize in a greenhouse or nursery setting. In another embodiment, the plantlets are transferred to a supplemented plant growth medium that optionally contains a plant growth regulator in a concentration that does not inhibit plant growth or kill the plant. Generally the supplemented plant growth medium does not contain a plant growth regulator. In this variation, the plantlet is grown, for example in WPM, sugar compound, and gelling agent for between about 1 week and about 12 weeks. In one variation, the plantlet is grown in such a supplemented plant growth medium for between about 2 weeks and about 8 weeks; in another variation, the plantlet is grown for between about 2 weeks and about 6 weeks.

The present application is further directed to a method for the propagation of Alexandrian laurel, comprising: (a) germinating an Alexandrian laurel seed using in vitro techniques; (b) culturing the germinated seed in a growth medium comprising a phenylurea cytokinin plant growth regulator to yield multiple shoots from a single seed; (c) separating the multiple shoot crown from the root(s), (d) culturing the crown in a basic medium comprising a substrate and basal medium; (e) culturing an individual shoot, isolated from the crown, in a root growth medium and (f) acclimatizing the plantlet comprising a shoot and a root in soil.

The present application is also directed to a method to produce multiple seedlings of Alexandrian laurel from one seed, the method comprising: (a) germinating an Alexandrian laurel seed in a germination induction medium including gibberellic acid at a concentration of about 4 ppm to about 15 ppm; (b) culturing the germinated seed in a growth induction medium including between about 1 µM and about 20 µM thidiazuron, wherein the culturing results in two or more shoots and at least one root visible from the seed; (c) separating the multiple-shoot crown from the root(s); (d) culturing the separated multiple-shoot crown in a basic medium; (e) isolating an individual shoot from the multiple shoot crown and culturing the shoot in a root growth medium including a plant growth regulator to yield a plantlet having a viable shoot and root; and (f) acclimatizing the plantlet in soil.

In one embodiment, the seed is germinated for at least about 4 weeks, optionally at least about 8 weeks; the germinated seed is cultured for at least about four weeks, optionally at least about 8 weeks; and the basic medium is a supplemented Woody Plant medium and the multiple shoot crown is cultured therein for at least about two months, optionally at least about three months. In another embodiment, the supplemented Woody Plant medium includes between about 1% and about 1.5% by weight sucrose. In another embodiment, the plant growth regulator is between about 0.1 mg/L and about 5 mg/L IBA (indole-3-butyric acid) and the individual shoot is cultured therein for at least about two weeks, optionally at least about 4 weeks. In yet another embodiment, the method further comprises repeating steps (d), (e) and (f) as described herein. In one variation of any disclose aspect or embodiment, the step of acclimatizing the plantlet in soil includes the step of acclimatizing in soil within a greenhouse.

The present application is further directed to a method to produce multiple seedlings of Alexandrian laurel from one seed, the method comprising: (a) germinating an Alexandrian laurel seed in a germination induction medium including gibberellins; (b) culturing the seed in a growth medium comprising a phenylurea cytokinin plant growth regulator for a sufficient time to grow two or more visible shoots; (c) separating the multiple shoot crown from the root system; (d) culturing the multiple shoot crown in a growth medium comprising a basal medium and optionally a sugar compound and/or a plant growth regulator; (e) separating an individual shoot from the multiple shoot crown; (f) culturing an individual shoot in a root growth medium comprising an auxin plant growth regulator until a viable root is observed; (g) acclimatizing the resulting plantlet in soil. The appropriate steps in this method can be repeated with each individual shoot that grows from a multiple shoot crown. The multiple shoot crown can be kept in a basic medium optionally comprising a plant growth regulator.

In one variation, the phenylurea cytokinin plant growth regulator is thidiazuron, usually at a concentration of between about 0.5 mg/L and about 4 mg/L, generally at a concentration of about 1.0, about 2.0 or about 3.0 mg/L.

In one embodiment, after the germinated seed grows for an appropriate length of time in supplemented plant growth medium containing a phenyl urea cytokinin, multiple shoots grow from a single seed. In this example, the germinated seed is allowed to grow in the supplemented plant growth medium containing a phenyl urea cytokinin for between about 2 weeks and about 10 weeks before further treatment. Alternately, the germinated seed is allowed to grow in the medium for between about 3 weeks and 8 weeks. Generally, the germinated seed is allowed to grow for between about 4 weeks and 6 weeks. Usually, the multiple-shoot plantlet is removed from the supplemented plant growth medium and the crown, comprising multiple shoots, is cut from the root, which may or may not comprise brown root growth tips. The crown is transferred to a supplemented growth media, comprising, for example, WPM, a sugar compound and a gelling agent. In one embodiment, the supplemented basal medium is a supplemented WPM.

In one embodiment, the multiple-shoot crown is allowed to grow in a supplemented growth medium for at least about 2 weeks. In one variation, the supplemented growth medium contains a plant growth regulator; in another variation, the supplemented growth medium does not contain a plant growth regulator. Generally, the multiple-shoot crown is allowed to grow in the medium for between about 1 month and 5 months. Alternately, the multiple-shoot crown is allowed to grow for between about 2 months and 4 months. In one variation, the multiple-shoot crown is allowed to grow for between about 10 weeks and 14 weeks in the supplemented growth medium.

Generally, after about 3 months of growth in the supplemented growth medium, which optionally contains a plant growth regulator, the dominant shoots are individually isolated from the multiple-shoot crown. Generally, a single shoot is cut away from a multiple-shoot crown. After removal, each shoot is individually transferred to a supplemented plant rooting medium containing an auxin. The residual multiple-shoot crown is then returned to the supplemented plant growth medium optionally containing a plant growth regulator. When additional dominant shoots are observed, each dominant shoot is individually isolated from the original multiple-shoot crown. The growth/isolation process is repeated until no further dominant shoots are observed growing from the crown.

Each isolated shoot is allowed to grow in a supplemented growth medium comprising an auxin for at least about 2 weeks, generally for between about 2 weeks and 8 weeks. In one variation, the isolated shoot is allowed to grow for between about 3 weeks and 5 weeks, usually about 4 weeks before being transferred to soil. The supplemented plant growth medium comprising an auxin optionally further comprises one or more of a sugar compound, agar and activated charcoal. Generally the basic medium, such as WPM, is prepared at half-strength and the pH is adjusted to between about 5.5 and about 6.0, usually at about 5.8 before the addition of agar. In one variation, the sugar compound concentration is about 0.5% to about 3% by weight; in another variation the concentration is about 1% to about 1.5% by weight. In one variation, the auxin concentration is about 0.25 mg/L to about 2 mg/L; in another variation, the auxin concentration is about 0.5 mg/L to about 1.0 mg/L. Alternately, the auxin is indole-3-butyric acid at a concentration of about 0.5 mg/L, 1.0 mg/L or 1.5 mg/L. In one variation, the activated charcoal comprises at least about 0.25% by weight; in another variation, the charcoal concentration is about 0.5% to about 1.0% by weight.

Generally the isolated shoot is grown in the supplemented plant growth medium containing an auxin until a root grows to between about 1.5 cm and about 3 cm in length. At this point, it is propitious to transfer the plantlet having a viable shoot and root to soil to acclimatize in a greenhouse or nursery setting.

In another aspect, the present application discloses a method of propagating multiple Alexandrian laurel plantlets from a single seed, the method comprising: (a)disinfecting an Alexandrian laurel seed; (b) germinating the seed for at least about eight weeks in a germination induction medium including gibberellic acid at a concentration of about 4 ppm to about 15 ppm; (c) culturing the germinated seed for at least about four weeks in a growth induction medium including between about 1 μM and about 20 μM thidiazuron, wherein the culturing results in at least one root and a multiple shoot crown comprising a first individual shoot and a second individual shoot visible from the seed; (d) separating the first individual shoot and the second individual shoot from the root(s); (e) culturing the first individual shoot and the second individual shoot in a root growth medium including a plant growth regulator to yield a first plantlet and a second plantlet, each plantlet having a viable shoot and root; and (f) acclimatizing the first and second plantlets in soil.

In one embodiment, the disinfectant includes an active ingredient selected from bleach, methanol, ethanol and combinations thereof. In another embodiment, the separating step further includes a preceding step of selecting a dominant shoot. In yet another embodiment, the plant growth regulator is an auxin.

Overview

As described herein, an efficient aseptic germination protocol was developed for Alexandrian laurel. The micropropagated plantlets produced from the methods described demonstrate more vigorous growth with healthier looking and more abundant roots compared to conventional germination methods. In particular the micropropagated plantlets of the present application are characterized by a balanced seedling growth; the abundant root system of the plantlets is a strong indicator of health and vigor of the plantlets. In one example two-year old micropropagated plantlets were as big as three to five-year old conventionally propagated plantlets.

Seedling growth and production of multiple shoots per seed were balanced by the addition of plant growth regulators to the culture medium at timely points in the production process. In one example, early growth after the initial seed germination in the presence of BA resulted in balanced seedling development by simultaneously promoting shoot growth and slowing down root growth. In another example, early growth after the initial seed germination in the presence of TDZ enabled multiple seedling production per seed by producing multiple shoots (5-10 shoots per seed).

Applicants also identified an earlier-than-expected developmental stage for successful acclimatization of micropropagated seedlings to a greenhouse or nursery environment. Conventional wisdom suggests waiting until the plantlet has more substantial shoot growth before the transition to soil in a nursery or greenhouse. Applicants have determined one alternative for a successful acclimatization of an Alexandrian laurel seedling micropropagated using a purin-based cytokinin that the developmental stage when a single true leaf and at least about 2 cm to about 3 cm of roots have been observed, is a propitious time to transfer the plantlet to soil. Applicants have further determined another alternative when generating multiple shoots using phenyl urea cytokinin, that after the isolated shoot has grown for about 1 month in the supplemented growth medium comprising an auxin, is a propitious time to transfer the plantlet to soil.

The present application is directed to a method for the propagation of Alexandrian laurel, comprising: (a) germinating an Alexandrian laurel seed using in vitro techniques; (b) culturing the germinated seed in a growth medium comprising a basal medium and a purin-based cytokinin plant growth regulator until a plantlet comprising at least one root and one leaf is visible; and (c) acclimatizing the plantlet in soil. In one variation, the substrate is agar and the basal medium is selected from the group consisting of Woody Plant Medium and MS medium. In one variation, the cytokinin is selected from the group consisting of 6-benzylaminopurine, kinetin, 2-isopentyladenine and zeatin, and mixtures thereof. In another variation, the cytokinin is selected from the group consisting of between about 1.0 mg/L and about 4.0 mg/L 6-benzylaminopurine. In another variation, the method further comprises washing and surface-sterilizing the seed before placing the seed in the growth induction medium. In another variation, the auxin is selected from the group consisting of indole-3-butyric acid, indole-3-acetic acid, and alpha-naphthaleneacetic acid, and mixtures thereof.

In another aspect, the present application is further directed to a method for the propagation of Alexandrian laurel, comprising: (a) germinating an Alexandrian laurel seed using in vitro techniques; (b) culturing the germinated seed in a growth medium comprising a phenylurea cytokinin plant growth regulator to yield multiple shoots from a single seed; (c) separating the multiple shoot crown from the root(s), (d) culturing the crown in a basic medium comprising a substrate and basal medium; (e) culturing an individual shoot, isolated from the crown, in a root growth medium and (f) acclimatizing the plantlet comprising a shoot and a root in soil. In one variation, the cytokinin is thidiazuron. In one embodiment, the method produces 10 or more seedlings from a single seed, alternately, 20 or more seedlings from a single seed, or 30 or more seedlings from a single seed.

EXAMPLES

Materials and Methods

Seeds were purchased (Gethsemane Garden and Landscape Services, Inc., Greensboro, N.C.) and disinfected in a 20% bleach solution plus 20 drops Tween-20 per liter for 20 minutes and then rinsed immediately 3 times with sterile purified water.

The disinfected seeds were subsequently transferred to test tubes containing agar medium and 10 ppm $GA_3$. The medium pH was adjusted to 5.8 with 1N KOH or 1 N HCl. The culture medium was sterilized by autoclaving at 121° C. (106 kPa) for 20 minutes.

All cultures described herein were transferred onto fresh media every 4 weeks and incubated in a plant tissue culture grade growth chamber under a 16-h photoperiod and a photo flux density of 37.6±4.8 $\mu mol\ s^{-1}m^{-2}$ light per day provided by cool white fluorescent tubes at 23±0.1° C., unless otherwise noted.

Example 1

The seeds were prepared according to Materials and Methods above. The seeds were kept in agar medium containing $GA_3$ for about 10 weeks, by which time a majority of the seeds had germinated.

Example 1A

Figure 1:
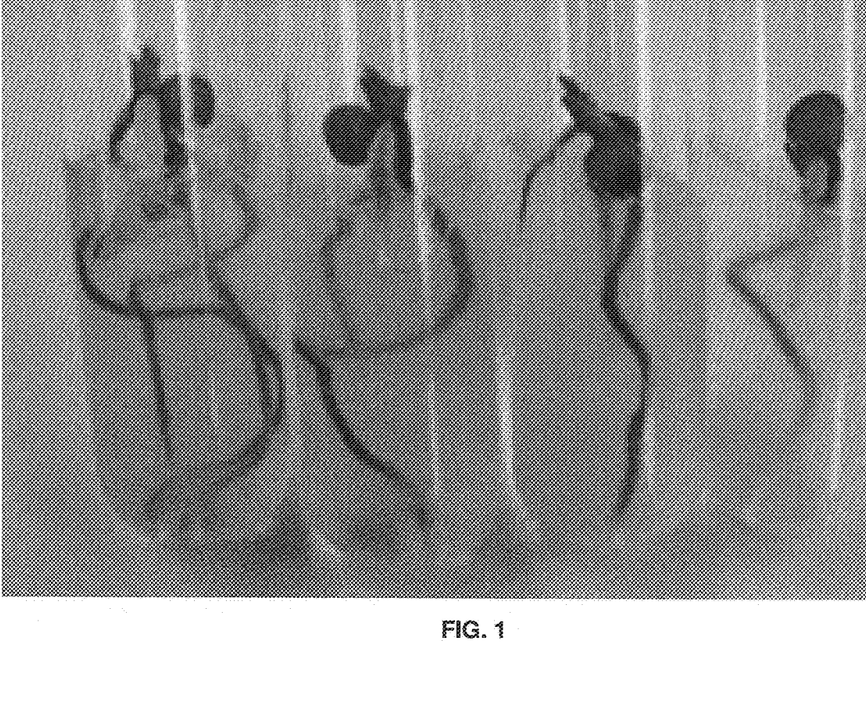
FIG. 1 shows Alexandrian laurel seedlings after germination in gibberellic acid ($GA_3$) supplemented agar medium, generally from 2-10 weeks.

At 10 weeks, a group of germinated seeds from Example 1 was removed from agar medium containing $GA_3$ with a lot of root growth and little shoot growth (See FIG. 1). The micropropagated plantlets were then potted in soil and transferred to a greenhouse.

Example 1B

At 10 weeks, a group of germinated seeds from Example 1 was removed from agar medium containing $GA_3$ and transferred to a supplemented WPM culture further comprising BA (at 1.0, 2.0, or 3.0 mg/L, respectively 4.44, 8.88, or 13.32 µM).

Figure 2:
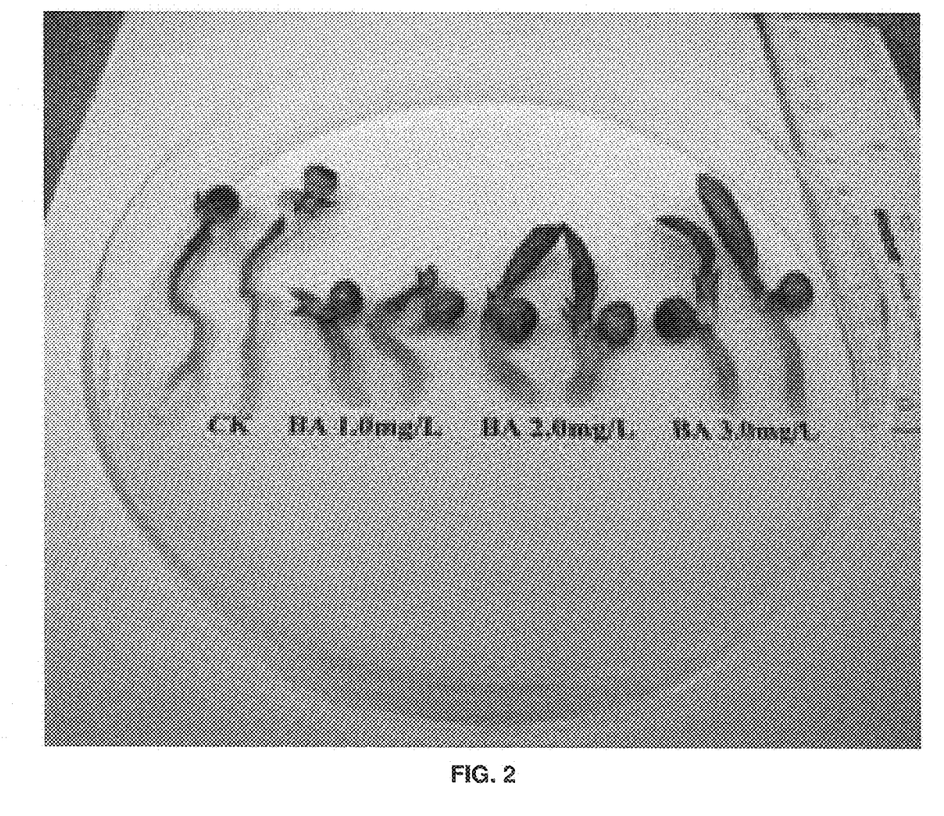
FIG. 2 shows Alexandrian laurel seedlings from benzyladenine (BA)-supplemented Woody Plant Medium after 4 weeks of treatment.

Compared to Example 1A, the young seedlings demonstrated more balanced shoot and root growth after growing in the presence of BA for about 4 weeks (see FIG. 2) before being transferred to soil.

Example 1C

At 10 weeks, a group of germinated seeds from Example 1 was removed from agar medium containing $GA_3$ and transferred to a supplemented WPM culture further comprising TDZ (at 1.0, 2.0, or 3.0 mg/L, respectively 4.54, 9.08, or 13.62 µM).

Figure 3:
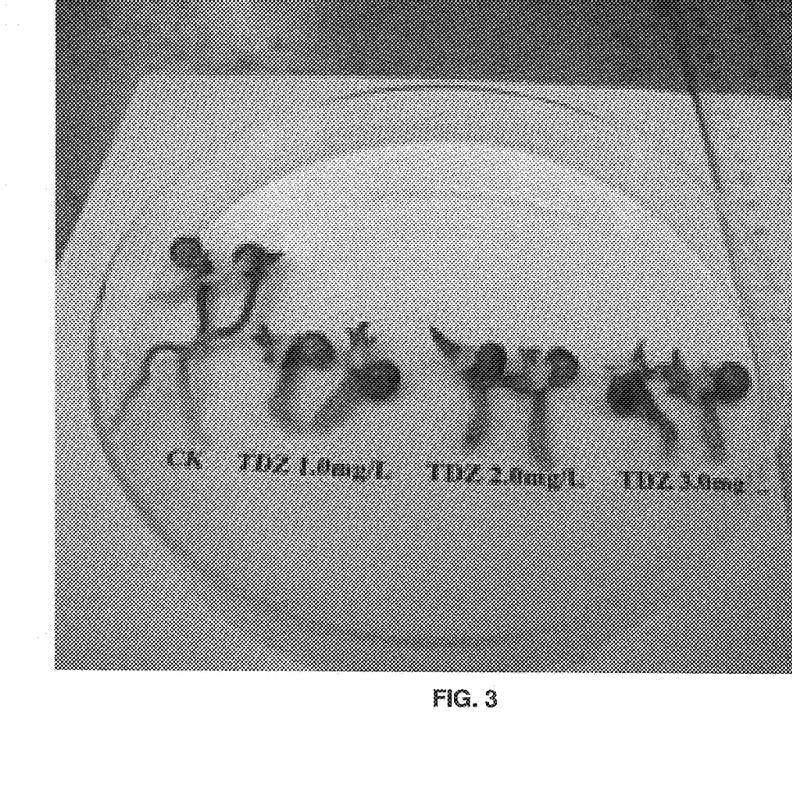
FIG. 3 shows Alexandrian laurel seedlings from thidiazuron (TDZ)-supplemented Woody Plant Medium after 50 days of treatment.

The young seedlings were cultured in the presence of TDZ for about 50 days (see FIG. 3), resulting in multiple shoots from each seed. After 50 days of treatment in a TDZ supplemented WPM, applicants observed that the root growth points began to turn brown.

Figure 4:
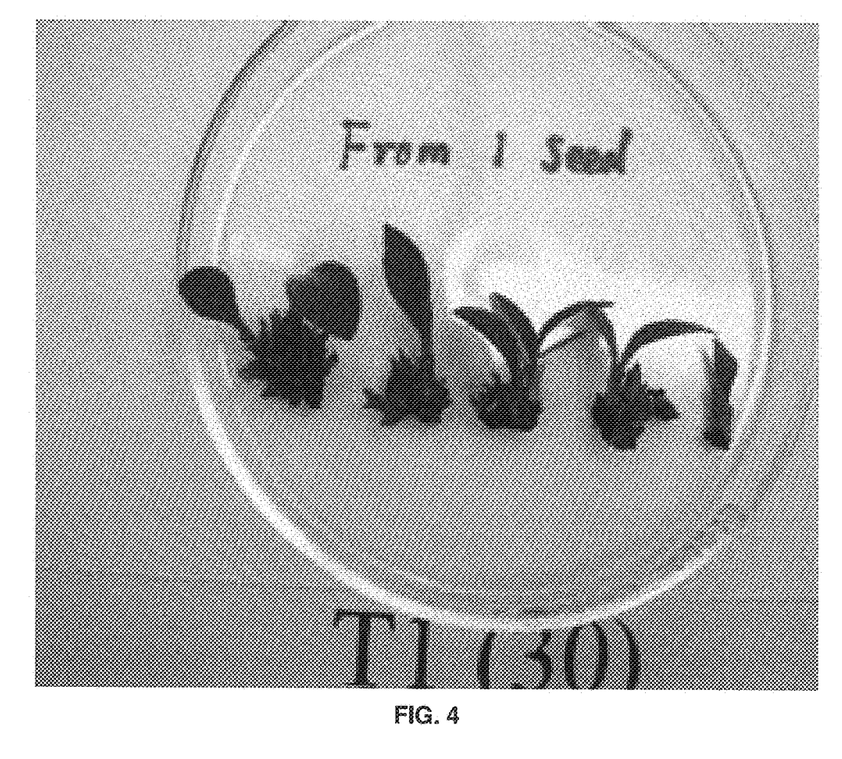
FIG. 4 shows a crown of Alexandrian laurel comprising multiple shoots from supplemented Woody Plant Medium after about 3 months of treatment.

The crown was cut away from the root system and was transferred to a supplemented WPM culture. The multiple-shoot crowns were allowed to grow in the supplemented WPM culture for about 3 months (see FIG. 4).

Figure 5:
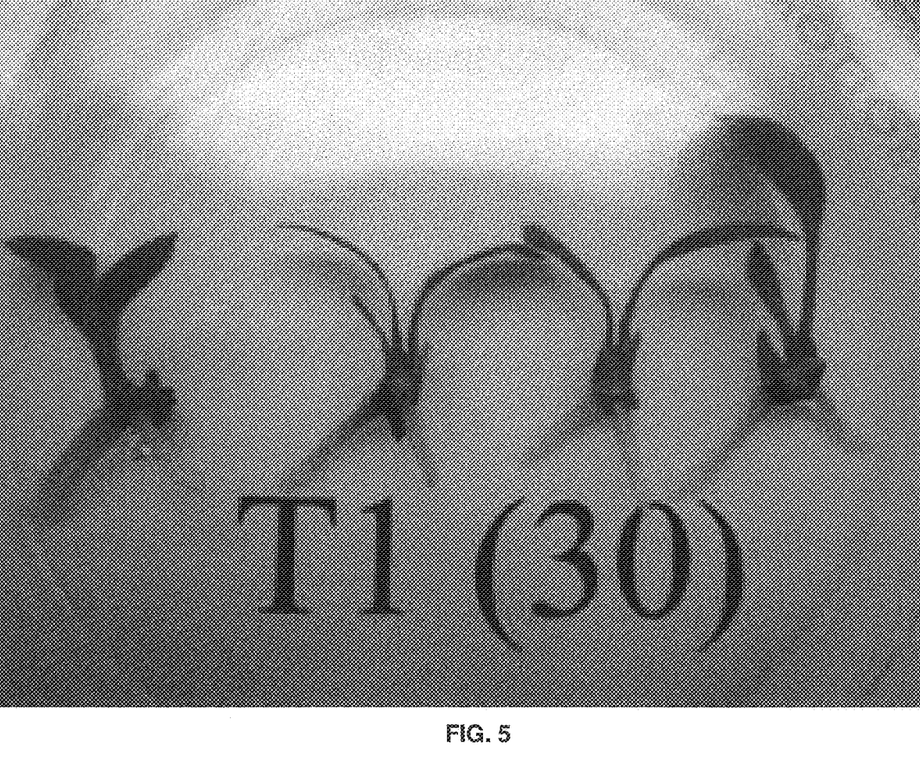
FIG. 5 shows Alexandrian laurel seedlings from indole-3-butyric acid (IBA)-supplemented Woody Plant Medium after about 4 weeks of treatment.

At three months, the dominant shoots were cut from the multiple-shoot crown under sterile conditions and individually placed in an additional plant growth culture. The culture comprised Woody Plant Medium at half concentration with supplements of sucrose (1% or 1.5% by weight) 0.7% agar, as well as IBA (0.5 mg/L or 1.0 mg/L, respectively 2.46 or 4.92 µM) and charcoal (0.5% or 1% by weight). The medium pH was adjusted to 5.8 with 1N KOH or 1 N HCl before agar was added. The dominant shoots were allowed to grow on the IBA-supplemented WPM medium for about 4 weeks (see FIG. 5). Then the micropropagated plantlets were transferred to the greenhouse potted in soil.

Upon removal of the dominant shoots from the multiple-shoot crown, each remaining crown that still contained multiple shoots was placed again in the supplemented WPM medium, comprising WPM, sucrose and agar as described above. Growth in this medium as allowed until identification of one or more dominant shoots, which were removed and treated as described above. This process yielded as many as 30 plantlets from a single seed.

Example 2

The seeds are prepared according to Materials and Methods above.

At 10 weeks, a group of germinated seeds from Example 1 is removed from the $GA_3$ supplemented WPM and transferred to a supplemented WPM culture further comprising kinetin (at 0.1, 0.5, 1.0, 1.5, 2.0, 2.5 or 3.0 mg/L, respectively 0.46, 2.32, 4.65, 6.97, 9.29, 11.62 or 13.94 µM).

The young seedlings are micropropagated in the presence of kinetin for 2-6 weeks. The micropropagated plantlets are then transferred to soil.

Example 3

The seeds are prepared according to Materials and Methods above.

At 10 weeks, a group of germinated seeds from Example 1 is removed from the $GA_3$ supplemented WPM and transferred to a supplemented WPM culture further comprising zeatin (at 0.1, 0.5, 1.0, 1.5, 2.0, 2.5 or 3.0 mg/L, respectively 0.46, 2.28, 4.56, 6.84, 9.12, 11.40 or 13.68 µM).

The young seedlings are micropropagated in the presence of zeatin for 2-6 weeks. The micropropagated plantlets are then transferred to soil.

Example 4

The seeds are prepared according to Materials and Methods above.

At 10 weeks, a group of germinated seeds from Example 1 is removed from the $GA_3$ supplemented WPM and transferred to a supplemented WPM culture further comprising BA (at 0.5, 1.0, 1.5, 2.0, 2.5 or 3.0 mg/L, respectively 2.22, 4.22, 6.66, 8.88, 11.10 or 13.32 µM) and kinetin (at 0.1, 0.5, 1.0, 1.5, 2.0, 2.5 or 3.0 mg/L, respectively 0.46, 2.32, 4.65, 6.97, 9.29, 11.62 or 13.94 µM).

The young seedlings are micropropagated in the presence of BA+kinetin for 2-6 weeks and then transferred to soil.

Example 5

The seeds are prepared according to Materials and Methods above.

At 10 weeks, a group of germinated seeds from Example 1 is removed from the $GA_3$ supplemented WPM and transferred to a supplemented WPM culture further comprising TDZ (at 0.5, 1.0, 1.5, 2.0, 2.5 or 3.0 mg/L, respectively 2.27, 4.54, 6.81, 9.08, 11.35 or 13.62 µM) and kinetin (at 0.1, 0.5, 1.0, 1.5, 2.0, 2.5 or 3.0 mg/L, respectively. 46, 2.32, 4.65, 6.97, 9.29, 11.62 or 13.94 µM).

The young seedlings are micropropagated in the presence of TDZ+kinetin for 4-8 weeks.

The crown is cut away from the root system and transferred to a supplemented WPM culture, comprising WPM, sucrose and agar as described above. The multiple-shoot crowns are allowed to grow in the supplemented WPM culture for about 3 months.

At three months, the dominant shoots are cut from the multiple-shoot crown under sterile conditions and individually placed in an additional plant growth culture. The culture comprises basal Woody Plant Medium at half concentration with supplements of sucrose (1% or 1.5% by weight) 0.7% agar, as well as IBA (0.5 mg/L or 1.0 mg/L, respectively 2.46 or 4.92 µM) and charcoal (0.5% or 1% by weight). The medium pH is adjusted to 5.8 with 1N KOH or 1 N HCl before agar is added. The dominant shoots are allowed to grow on the IBA-supplemented WPM medium for about 4 weeks (see FIG. 6). Then the micropropagated plantlets are transferred to the greenhouse potted in soil.

Upon removal of the dominant shoots from the multiple-shoot crown, each remaining crown that still contained multiple shoots is placed again in supplemented WPM medium with optional plant growth regulator. Growth in this medium as allowed until identification of one or more dominant shoots, which are removed and treated as described above.

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A method to produce multiple seedlings of Alexandrian laurel from one seed, the method comprising:
    (a) germinating an Alexandrian laurel seed in a germination induction medium including gibberellic acid at a concentration of about 4 ppm to about 15 ppm;
    (b) culturing said germinated seed in a growth induction medium including between about 1 µM and about 20 µM thidiazuron, wherein said culturing results in two or more shoots and at least one root visible from said seed;
    (c) separating said multiple-shoot crown from the root(s);
    (d) culturing said separated multiple-shoot crown in a basic medium;
    (e) isolating an individual shoot from said multiple shoot crown and culturing said shoot in a root growth medium including a plant growth regulator to yield a plantlet having a viable shoot and root; and
    (f) acclimatizing said plantlet in soil.

2. The method of claim 1, wherein
    (a) said seed is germinated for at least about four weeks
    (b) said germinated seed is cultured for at least about four weeks; and
    (c) said basic medium is a supplemented Woody Plant medium.

3. The method of claim 2, wherein said supplemented Woody Plant medium includes between about 1% and about 1.5% by weight sucrose.

4. The method of claim 1, wherein said plant growth regulator is between about 0.1 mg/L and about 5 mg/L IBA (indole-3-butyric acid).

5. The method of claim 1, further comprising repeating steps (d), (e) and (f).

6. The method of claim 1, wherein said step of acclimatizing said plantlet in soil includes the step of acclimatizing in soil within a greenhouse.

7. A method of propagating multiple Alexandrian laurel plantlets from a single seed, the method comprising:
    (a) disinfecting an Alexandrian laurel seed;
    (b) germinating said seed for at least about eight weeks in a germination induction medium including gibberellic acid at a concentration of about 4 ppm to about 15 ppm;
    (c) culturing said germinated seed for at least about four weeks in a growth induction medium including between about 1 µM and about 20 µM thidiazuron, wherein said culturing results in at least one root and a multiple shoot crown comprising a first individual shoot and a second individual shoot-visible from said seed;
    (d) separating said first individual shoot and said second individual shoot from the root(s);
    (e) culturing said first individual shoot and said second individual shoot in a root growth medium including a plant growth regulator to yield a first plantlet and a second plantlet, each plantlet having a viable shoot and root; and
    (f) acclimatizing said first and second plantlets in soil.

8. The method of claim 7 wherein said step of disinfecting said seed includes the step of employing a disinfectant including an active ingredient selected from bleach, methanol, ethanol and combinations thereof.

9. The method of claim 7 wherein said separating step further includes a preceding step of selecting a dominant shoot.

10. The method of claim 7 wherein said plant growth regulator is an auxin.

* * * * *

UNITED STATES PATENT AND TRADEMARK OFFICE
CERTIFICATE OF CORRECTION

| | | |
|---|---|---|
| PATENT NO. | : 9,474,272 B1 | Page 1 of 1 |
| APPLICATION NO. | : 13/838725 | |
| DATED | : October 25, 2016 | |
| INVENTOR(S) | : Guochen Yang and Zhongge Lu | |

It is certified that error appears in the above-identified patent and that said Letters Patent is hereby corrected as shown below:

In the Specification

Column 1, Line 4 should read:

Statement As To Rights To inventions Made Under Federally Sponsored Research Or Development

This invention was made with government support under Grant Number 2010-33100-08912/0219532, awarded by the United States Department of Agriculture, National Institute of Food and Agriculture. The United States Government has certain rights in the inventions.

Signed and Sealed this
Twenty-first Day of February, 2017

Michelle K. Lee
*Director of the United States Patent and Trademark Office*